(12) United States Patent
Fronabarger et al.

(10) Patent No.: US 7,375,221 B1
(45) Date of Patent: May 20, 2008

(54) METHOD FOR AZIDOAMINOTRIAZOLE, NITROSOGUANAZINE, AND RELATED COMPOUNDS

(75) Inventors: John William Fronabarger, Sun Lakes, AZ (US); Michael E. Sitzmann, Adelphi, MD (US); Michael D. Williams, Gilbert, AZ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/268,408

(22) Filed: Oct. 31, 2005

(51) Int. Cl.
 *C07D 251/54* (2006.01)
 *C07D 249/14* (2006.01)
(52) U.S. Cl. .................... 544/197; 548/265.2
(58) Field of Classification Search ............. 548/264.8, 548/265.2; 544/194, 197
See application file for complete search history.

(56) References Cited

OTHER PUBLICATIONS

R.M.Herbst and J.A. Garrison, J. Org. Chem., vol. 18, 941 (1953).
Kofman, T.P., Kartseva, G. Yu., Namestnikov, V.I., Paketina, E. A., Russ. J. Org. Chem. 1998, 34 (7), 1032 (translated from Zh. Org. Khim., 1998 34 (7), 1084).
Kofman, T.P., Russ. J. Org. Chem. 2001, 37 (8), 1158(translated from Zh. Org. Khim., 2001 37 (8), 1217).

*Primary Examiner*—Rebecca L Anderson
*Assistant Examiner*—Robert Havlin
(74) *Attorney, Agent, or Firm*—Fredric J. Zimmerman

(57) ABSTRACT

The present invention includes a method of making of azidoaminotriazole (5-azido-2H-[1,2,4]triazol-3-ylamine), nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine), novel nitrosoguanazine salts, azidonitraminotriazole/salts and the making of azidonitraminotriazole and salts, and novel metal complexes of an azidonitramine (4,6-diazido-N-nitro-1,3,5-triazin-2-amine) and the making of these metal complexes of this azidonitramine. Azidoaminotriazole, nitrosoguanazine, and azidonitramine compounds, their intermediates, and their salts may generally relate to energetic compounds, while nitrosoguanazine compounds and their metal salts may also have commercial potential in biomedical and pharmaceutical applications.

29 Claims, No Drawings

METHOD FOR AZIDOAMINOTRIAZOLE, NITROSOGUANAZINE, AND RELATED COMPOUNDS

STATEMENT OF GOVERNMENT INTERESTS

The invention described herein may be manufactured and used for the Government of the United States of America for governmental purposes without payment of any royalties thereon or therefore.

FIELD OF THE INVENTION

The present invention generally relates to the making of azidoaminotriazole (5-azido-2H-[1,2,4]triazol-3-ylamine), the making of a dimer of nitrosoguanazine ($N^3$-[(1E)-3-(4,5-diamino-4H-1,2,4-triazol-3-yl)-1,2-dioxidotriaz-1-enyl]-4H-1,2,4-triazole-3,4,5-triamine), novel nitrosoguanazine salts and the making of these nitrosoguanazine salts, azidonitraminotriazole/salts and the making of azidonitraminotriazole and salts, and novel metal complexes of an azidonitramine (4,6-diazido-N-nitro-1,3,5-triazin-2-amine) and the making of these metal complexes of this azidonitramine. Azidoaminotriazole, nitrosoguanazine, and azidonitramine compounds, their intermediates, and their salts may generally relate to energetic compounds, while nitrosoguanazine compounds and their metal salts may also have commercial potential in biomedical and pharmaceutical applications.

BACKGROUND OF THE INVENTION

"Energetic" compounds are used extensively in a wide variety of applications, e.g., in rocket propellants, explosive formulations, and the inflation of automobile and aircraft occupant restraint bags. It is generally preferred that such compounds have a high energy content yet be relatively insensitive to impact, so that accidents are avoided and energy is released only when intended. The requirements of insensitivity and high energy are in conflict, making the development of new energetic compounds a difficult and challenging synthetic problem.

Previously known energetic compounds can possess one or more disadvantages, e.g., they are overly impact-sensitive, difficult to synthesize on a large scale, or not sufficiently energetic. Typically, energetic compounds used to inflate occupant restraint bags in automobiles or aircraft contain potentially toxic heavy metal initiating materials, e.g., lead styphnate.

The present invention provides a class of compounds, i.e., azidoaminotriazole, various salts and complexes of nitrosoguanazine, and azidonitramines, that may have potential as propellants, explosives and initiating materials, including laser initiated materials, and that do not contain toxic heavy metals.

In addition, it is anticipated that nitrosoguanazine compounds and their metal salts may undergo denitrosation in the body, releasing nitric oxide. The nitrosoguanazine compounds and their metal salts may accordingly be used as biomedical and pharmaceutical agents, i.e., as so-called "NO-donors." NO donors are useful as vasodilating agents, insofar as NO activates guanylyl cyclase, increasing intracellular levels of cyclic guanosine 3',5'-monophosphate (cGMP) and CGMP brings about smooth muscle relaxation. Previously known NO donors include, for example, nitroglycerin (glyceryl trinitrate), isosorbide dinitrate, isosorbide-5-mononitrate, erythrityl tetranitrate, pentaerythritol tetranitrate, sodium nitroprusside, S-nitroso-N-acetylpenacillamine (SNAP), linsidomine chlorohydrate (also known as SIN-1), and the so-called "NONOates," complexes of nitric oxide and nucleophiles that contain the $N_2O_2$-group and release NO upon heating or hydrolysis without need for activation. The biomedical and pharmaceutical application of many known NO donors is limited, however, as a result of unwanted side effects, an undesirable NO release profile, or the like. Thus, there is a continuing need in the art for novel biomedical and pharmaceutical agents useful as vasodilators.

Russian workers refer to azidoaminotriazole in two articles, but do not provide a method of making or any properties of this material: (1) Kofman, T. P., Kartseva, G. Yu., Namestnikov, V. I., and Paketina, E. A., *Russ. J. Org. Chem.* 1998, 34 (7), 1032 (translated from *Zh. Org. Khim.*, 1998, 34 (7), 1084); and (2) Kofman, T. P., *Russ. J. Org. Chem.* 2001, 37 (8), 1158 (translated from *Zh. Org. Khim.*, 2001, 37 (8), 1217). Currently, there is no known preparation for azidoaminotriazole in the literature.

The conversion of amines to diazonium salts via primary nitrosoamines is known. However, because primary nitrosoamines so readily convert to diazonium salts, it is quite difficult to isolate these primary nitrosoamine materials. Consequently, primary nitrosoamines have been very limited in their availability for other uses. Reports of isolation of primary nitrosoamines in the literature are rare. One report by H. Gehlen and J. post, *Liebigs in Ann. Chem.*, Bd. 665 (1963), pages 144-149, describes the preparation of 3-nitrosamino-4-aryl-5-alkyl-1,2,4-triazoles. However, their starting materials, 3-amino-4-aryl-5-alkyl-1,2,4-triazoles, contain only one reactive amine. The starting material of the present invention, guanazine (3,4,5-triamino-1,2,4-triazole), on the other hand, may contain three reactive amines and may allow the selective preparation of a primary nitrosoamine in the presence of other reactive amines in the same molecule.

SUMMARY OF THE INVENTION

An aspect of an exemplary embodiment of the present invention includes a method of making for azidoaminotriazole (5-azido-2H-[1,2,4]triazol-3-ylamine), which may have potential as an energetic high-nitrogen propellant, explosive, and/or gas generator.

Another aspect of an exemplary embodiment of the present invention includes the use of azidoaminotriazole as an intermediate in the formation of azidonitraminotriazoles and salts, azo and azoxy linked azidotriazoles and salts and triazene linked azidotriazoles and salts, which may have potential as energetic high-nitrogen propellants, initating explosives, and/or gas generators.

Yet another aspect of an exemplary embodiment of the present invention includes the method of making numerous acid salts of azidoaminotriazole, including energetic acid salts, e.g., nitric and perchlorate salts, which may have potential as energetic high-nitrogen propellants, explosives, gas generators, or initiating explosives with high thermal stabilities.

Yet another aspect of an exemplary embodiment of the present invention includes the conversion of nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) to various salts, including copper salt complexes that may contain nitrate or perchlorate ions, which may have potential as energetic high-nitrogen propellants, explosives, and/or gas generators.

Yet another aspect of an exemplary embodiment of the present invention includes the method of making numerous nitrosoguanazine compounds and/or metal salts for biomedical and pharmaceutical applications.

Yet another aspect of an embodiment of the present invention includes the method of making of 2,4-diazido-6-nitramino-[1,3,5]-triazine and alkali metal salts of 2,4-diazido-6-nitramino-[1,3,5]-triazine.

DETAILED DESCRIPTION OF EXEMPLARY EMBODIMENTS OF THE INVENTION

An aspect of an exemplary embodiment of the present invention includes the method of making azidoaminotriazole (4), which may be produced directly from guanazine (1) without isolation of the intermediate nitrosoguanazine (2), by using two or more equivalents of acid (HX) and one equivalent of sodium nitrite, as illustrated in Scheme 1, below. This process may proceed through the formation of nitrosoguanazine (2) and the diazonium salt (3). However, this process may produce a significant amount of by-products that are not easily removed from the desired product, azidoaminotriazole (4).

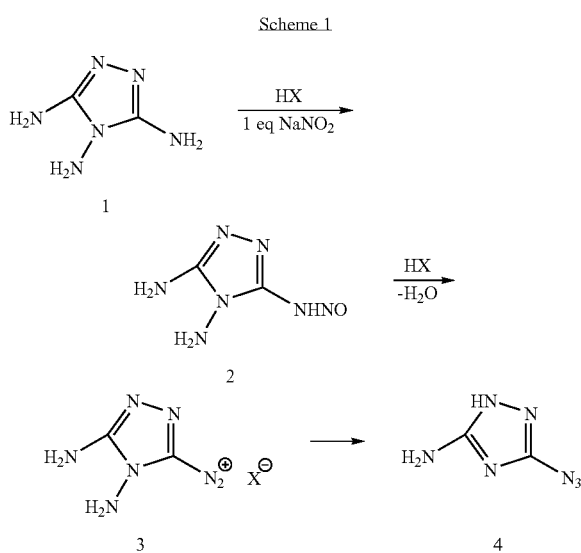

When one equivalent of acid, i.e., HX, is employed, the nitrosoguanazine may be isolated. Azidoaminotriazole may exist as three possible tautomers. Single crystal X-ray diffraction analysis of (4) crystallized from water indicates this product to be the tautomer with H on ring N next to the amino group.

Nitrosoguanazine (2) may potentially exist in other forms such as the dimer (2a), the N=NOH form (2b), etc., as illustrated in Scheme 2, below.

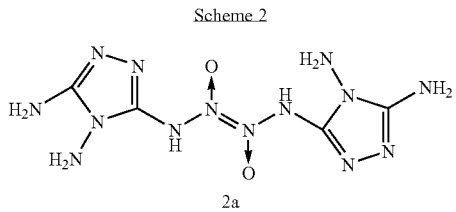

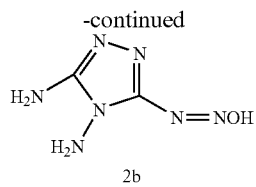

Experimental results indicate that based on its very low solubility in water, the isolated nitrosoguanazine is possibly the dimer (2a). The dimer (2a) may be converted to high-purity azidoaminotriazole by heating in water or dilute aqueous acid, as illustrated in Scheme 3, below.

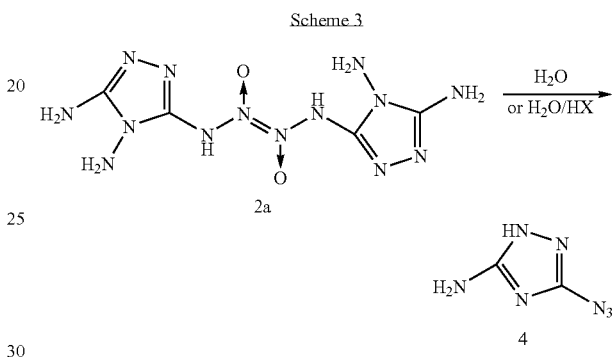

Alternatively, the dimer (2a) may be converted to the sodium (5a) and potassium (5b) salts of the monomer by treatment with sodium hydroxide and potassium hydroxide, respectively, as illustrated in Scheme 4, below. Single crystal X-ray diffraction analyses of such a salt may indicate that the nitroso group of nitrosoguanazine (2) is on an amino group attached to carbon. Therefore, the nitrosoguanazine (2) may be structured as ($N^3$-nitroso-4H-1,2,4-triazol-3,4,5-triamine), as shown by (5a) and (5b).

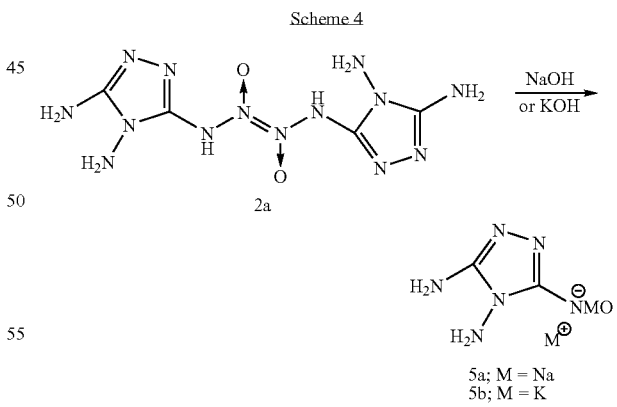

Treatment of 5a or 5b with copper (II) nitrate hemipentahydrate or copper (II) perchlorate hexahydrate may produce copper salt complexes containing nitrate and perchlorate anions, respectively. These copper salt complexes are green in color and may have potential use as laser-sensitive initiating materials. Copper (II) sulfate pentahydrate may produce the corresponding sulfate complex. Other possible energetic counter-ions may include dinitramide, chlorate, bromate, nitrite, etc. Other non-energetic counter-ions could include chloride, acetate, bromide, formate, salicylate, etc. Other metal salts such as iron, cobalt, nickel, zinc, etc. may also be used to form complexes with the nitrosoguanazine anion.

The nitrosoguanazine compounds and their metal salts may also be useful as biomedical and pharmaceutical agents. Such compounds and their metal salts may be used to treat NO-responsive disorders and conditions in humans and animals when the N-nitroso group undergoes denitrosation in the body, promoting vasodilation.

Referring to Scheme 5 below, azidoaminotriazole, nitric acid salt (6) may be treated with concentrated sulfuric acid to effect its conversion to azidonitraminotriazole (7). The azidonitraminotriazole (7) may be converted to the monopotassium salt (8) by neutralizing with one equivalent of potassium hydroxide. By using two equivalents of potassium hydroxide, the di-potassium salt may be formed.

Scheme 5

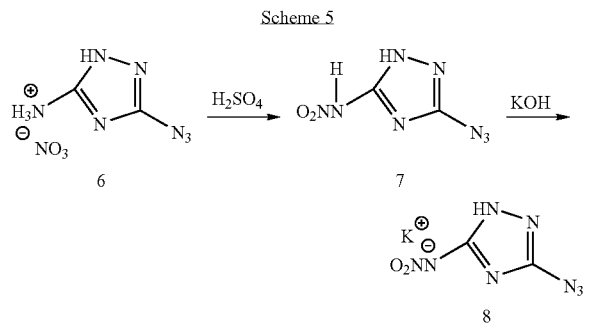

Referring to Scheme 6, below, 6-amino-2,4-diazido-[1,3,5]-triazine (10) may be prepared in two steps from cyanuric chloride (9) via 6-amino-2,4-dichloro-[1,3,5]-triazine. Treatment of the 6-amino-2,4-diazido-[1,3,5]-triazine with 100% nitric acid may produce the nitramine (11a), which may conveniently be converted to the corresponding cesium (11b) or rubidium (11c) complex by reaction with the appropriate metal hydroxide. Other metal complexes may also be available using these techniques. Experimental results indicate that these metal complexes demonstrate unusual behavior in solution, as is evidenced by the $^{13}C$ NMR spectra acquired in DMSO-$d_6$. The free acid (11a) has 5 peaks (150-171 ppm) indicating a mixture of diazido- and the cyclized azidotetrazolo-triazine, while the Rb salt (11c) has 3 peaks in the same region indicating complete cyclization. The increased ability of the Rb salt to cyclize is ascribed to higher electron density in the triazine ring compared to the free acid.

Scheme 6

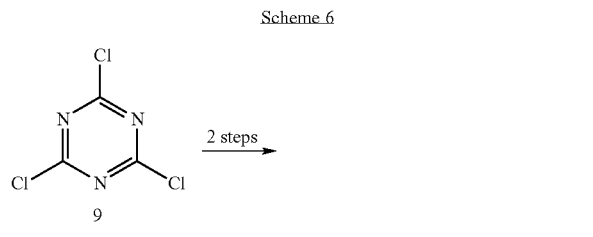

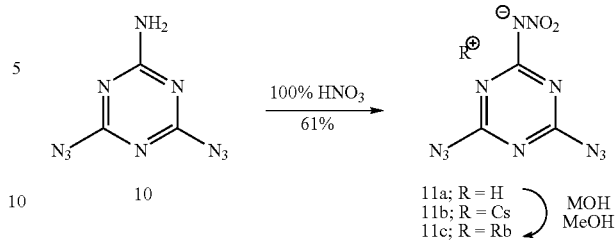

EXPERIMENTAL (ACTUAL) RESULTS

Examples 1-4 generally relate to a method of making azidoaminotriazole (5-azido-2H-[1,2,4]triazol-3-ylamine) (4) from a dimer of nitrosoguanazine ($N^3$-[(1E)-3-(4,5-diamino-4H-1,2,4-triazol-3-yl)-1,2-dioxidotriaz-1-enyl]-4H-1,2,4-triazole-3,4,5-triamine) (2a) and a method of making the dimer of nitrosoguanazine.

Example 1

The Method of Making Azidoaminotriazole (5-azido-2H-[1,2,4]triazol-3-ylamine)(4) from Guanazine ([1,2,4]triazole-3,4,5-triamine) (1)

In an exemplary embodiment of the present invention, guanazine (1) (approximately 0.90 g, 7.9 mmol) may be dissolved in about 18 ml of distilled water at 23° C. and the resulting solution then stirred and cooled in an ice bath. Sodium nitrite (approximately 0.54 g, 7.9 mmole) may then be added. After the sodium nitrite dissolves, a solution of acetic acid (approximately 1.50 g, 25 mmole) in about 6 ml of distilled water may be slowly added, dropwise over about 30 minutes. The solution may be held at an ice bath temperature for about one hour before it is allowed to warm to about 22° C. over about one and a half hours. After about 30 minutes at about 22° C., a red-orange precipitate may be removed by filtration and washed twice with about 2 ml of water. The red-orange precipitate may weigh approximately 0.38 g after air-drying. The filtrate may then be extracted 3× with about 20 ml of ethyl acetate. The solvent may be removed from the combined ethyl acetate extracts to give approximately 0.36 g (approximately 37% yield) of azidoaminotriazole (4) (mp approximately 160-165° C., decomposition) that contained small amounts of impurities by TLC and $^1H$ NMR analyses. TLC: $R_F$ of (4)=0.63 (chloroform/methanol/acetic acid, 40/8/1, v/v/v as developer). See $^1$HNMR and $^{13}C$ NMR in Example 3, below.

The red-orange precipitate may contain very little azidoaminotriazole (4) by TLC analysis. The main component may be a yellow by-product that may be extracted into hot methanol. This yellow by-product may precipitate as a methanol solvate upon cooling. The yellow by-product has a melting point of about 160° C., with very rapid decomposition. Other analytical values of the yellow by-product may be as follows: TLC: $R_F$=0.30 (chloroform/methanol/acetic acid, 40/8/1, v/v/v as developer); IR (ATR): 3500-3800, 2141 (medium), 1360,1327 (medium strong), 1209 (strong) cm$^{-1}$; $^1H$ NMR (DMSO-$d_6$): 5.80 (s, 2H), 6.37 (s, 2H), 12.38 (s, 1H), 12.81 (s, 1H) with peaks for methanol at 3.15 and 4.09; and $^{13}C$ NMR (DMSO-$d_6$): 152.5, 156.0, 162.1 (broadened) with a peak for methanol at 49.0.

Example 2

The Method of Making a Dimer of Nitrosoguanazine ($N^3$-[(1E)-3-(4,5-diamino-4H-1,2,4-triazol-3-yl)-1,2-dioxidotriaz-1-enyl]-4H-1,2,4-triazole-3,4,5-triamine) (2a)

In another exemplary embodiment of the present invention, guanazine ([1,2,4]triazole-3,4,5-triamine) (1) (5.4 g, 0.0473 mole) may be dissolved in about 90 ml of distilled water at about 23° C. and the solution may then be stirred and cooled in an ice bath. Sodium nitrite of approximately 97% purity (approximately 3.36 g, 0.0487 moles) may be added to the solution. After the sodium nitrite is dissolved, a solution of acetic acid of 99+ % purity (approximately 2.92 g, 0.0487 mole) in about 54 ml of distilled water may be added, dropwise over about ten minutes. The flask may then be stoppered and stirring in the ice bath may be continued for about one hour. The ice may then be removed and the bath may be allowed to warm to about 23° C. over about two hours. The mixture, which now contains some yellow precipitate, may be stirred for about an additional hour at about 23-24° C. before the stirring is stopped. The mixture may be allowed to stand overnight, e.g., about 17 hours, in a water bath at about 22-24° C. The yellow precipitate of guanazine (2a) may be removed by filtration and washed 4× with about 20 ml of cold water. The resulting product may then be air dried at room temperature overnight to yield approximately 4.87 g (72%), with a melting point of about 143° C., decomposition. Other analytical values of the resulting product may be as follows: $^1$H NMR (DMSO-$d_6$): 5.68 (s, 2H), 6.28 (s, 2H) 13.8 (broad); and IR (ATR): 3301, 3171, 1680 (strong), 1636, 1564, 1504, 1256 (strong), 1146, 1067, 980, 901, 800, 752, 720 $cm^1$. Analysis: Calculated for $C_4H_{10}N_{14}O_2$: C, 16.79; H, 3.52; N, 68.51. Found: C, 16.69; H, 3.63; N, 68.29; DSC (20° C./min): Onset: 152; Peak: 154.

Example 3

The Method of Making Azidoaminotriazole (5-azido-2H-[1,2,4]triazol-3-ylamine)(4) from Nitrosoguanazine Dimer ($N^3$-[(1E)-3-(4,5-diamino-4H-1,2,4-triazol-3-yl)-1,2-dioxidotriaz-1-enyl]-4H-1,2,4-triazole-3,4,5-triamine) (2a) in Water In yet another exemplary embodiment of the present invention, nitrosoguanazine (2a) (approximately 1.0 g, 0.0035 mole) may be stirred in about 30 ml of distilled water and the mixture may then be heated to about 70° C. over about 15 minutes and then may be held at about 70-75° C. for about 45 minutes. The mixture may then be cooled slightly before it is filtered to remove a small amount of a dark precipitate. This filtrate may then be extracted 5× with about 30 ml of ethyl acetate and the solvent may be removed from the combined ethyl acetate extracts to yield approximately 0.63 g (approximately 72% yield) of yellow crystals with a melting point of about 175° C., (decomposition) that were essentially pure azidoaminotriazole (4) by $^1$HNMR analysis. The azidoaminotriazole (4) may tend to retain some residual ethyl acetate but this may be removed by crystallization from water or methanol. Alternatively, removing volatiles from the filtrate under reduced pressure may yield crystals of azidoaminotriazole (4). Analytical results for this preparation of azidoaminotriazole (4) may be as follows: $^1$H NMR (DMSO-$d_6$): 6.31 (s, 2H), 11.91 (s, 1H); $^{13}$C NMR (DMSO-$d_6$): 154.39, 157.26; IR (ATR): 3420, 3398, 3161, 2147 ($N_3$, very strong), 1670, 1601, 1544 (strong), 1461, 1410, 1361, 1225, 1107, 718 $cm^{-1}$. Analyis: Calculated for $C_2H_3N_7$: C, 19.20; H, 2.42; N, 78.38. Found (crystals from water): C, 18.90; H, 2.42; N, 77.65. Found (crystals from methanol): C, 18.97; H, 2.41; N, 77.55; Differential Scanning Calorimetry (20° C./min): Onset: 174; Peak: 184.

Example 4

The Method of Making Azidoaminotriazole (5-azido-2H-[1,2,4]triazol-3-ylamine)(4) from Nitrosoguanazine Dimer ($N^3$-[(1E)-3-(4,5-diamino-4H-1,2,4-triazol-3-yl)-1,2-dioxidotriaz-1-enyl]-4H-1,2,4-triazole-3,4,5-triamine) (2a) in Water and Acetic Acid In yet another exemplary embodiment of the present invention, nitrosoguanazine (2a) (approximately 0.86 g, 0.003 mole) may be stirred in about 7 ml of distilled water and a solution of acetic acid (approximately 0.09 g, 0.0015 mole) in about 2 ml of water may then be added. This mixture may be heated to about 78-80° C. over about 15 minutes and then held at about 75-77° C. for about 45 minutes. The mixture may be cooled slightly before it is filtered to remove a small amount of dark solid that may be washed twice with about 2.5 ml of warm water. The volatiles may be removed from the filtrate under reduced pressure to yield approximately 0.71 g of a gummy yellow brown solid that is washed 3× with about 1.5 ml water to further yield 0.56 g (approximately 75% yield) of brownish yellow crystals of azidoaminotriazole (4). The water wash solution may be concentrated to give a second crop of 0.03 g, bringing the yield to approximately 79%.

Example 5 generally relates to the method of making acid salts of azidoaminotriazole (5-azido-2H-[1,2,4]triazol-3-ylamine) (4).

Example 5

The Method of Making Azidoaminotriazole (5-azido-2H-[1,2,4]triazol-3-ylamine), nitric acid salt (6)

In yet another exemplary embodiment of the present invention, azidoaminotriazole (4) (approximately 50 mg) may be stirred in about 5 ml of water, while the mixture is acidified by the slow addition of dilute (approximately 8%) nitric acid. All material dissolved and the water may be allowed to evaporate to yield a crystalline residue (approximately 60 mg). Analytical values for this crystalline residue may be as follows: $^1$H NMR (DMSO-$d_6$): 9.21 (bs); $^{13}$C NMR (DMSO-$d_6$): 149.55, 153.69; IR (ATR): 3430, 3338, 2738, (2202, 2165, $N_3$, weak), 1714 (medium strong), 1590, 1530, 1434, 1301 (strong), 1183, 1048, 1034, 1002, 843, 815, 803, 727, 707 $cm^{-1}$. Differential Scanning Calorimetry (20° C./min): Onset: 172; Peak: 174. Crystal structure analysis shows the product to be azidoaminotriazole, nitric acid salt (6). Analysis: Calculated for $C_2H_4N_8O_3$: C, 12.77; H, 2.14; N, 59.57. Found: C, 12.92; H, 2.31; N, 59.15.

The azidoaminotriazole nitric acid salt (6) may be expected to be useful as an intermediate towards the making of azidonitraminotriazole because analogously, nitraminotetrazole was prepared by dehydration of the aminotetrazole nitric acid salt with sulfuric acid by R. M. Herbst and J. A. Garrison as reported in *J. Org. Chem.*, 1953, 18, 941.

Examples 6-8 generally relate to the making of azidonitraminotriazole (3-azido-N-nitro-1H-1,2,4-triazol-5-amine)

(7) from azidoaminotriazole (5-azido-2H-[1,2,4]triazol-3-ylamine), nitric acid salt (6) and the conversion of the azidonitraminotriazole to mono- and di-potassium salts.

Example 6

The Making of Azidonitraminotriazole (3-azido-N-nitro-1H-1,2,4-triazol-5-amine) (7) from azidoaminotriazole (5-azido-2H-[1,2,4]triazol-3-ylamine), nitric acid salt (6)

In yet another exemplary embodiment of the present invention, the nitric acid salt of azidoaminotriazole (6) (approximately 0.17 g, 0.0096 mole) may be added in about 0.1 g portions over about 15 minutes to concentrated (about 95-98%) sulfuric acid (about 13 ml) and stirred well at about 3° C. in an ice bath. The resulting mixture may be stirred in the ice bath for about an additional 10 minutes before the mixture is allowed to warm to about 8-10° C. over about 20 minutes. The mixture may be held at about 8-10° C. for about 20 minutes and then poured onto ice (about 72 g). A yellow solution may be extracted twice with about 60 ml of ethyl acetate, followed by another course (3×) with about 50 ml of ethyl acetate. The combined extracts may be dried with sodium sulfate and the volatiles may then be removed under reduced pressure to give approximately 0.98 g of a yellow-orange solid. The yellow-orange solid may be stirred with about 10 ml of chloroform at about 25° C. to yield (0.88 g (approximately 54% yield) of azidonitraminotriazole (7). The azidonitraminotriazole (7) may be stirred in about 35 ml of water at about 25° C. to dissolve all but a very small amount of impurity that is removed by filtration. The water may be removed from the filtrate under reduced pressure to give 0.80 g of yellow-orange crystals. When heated, the crystals may deflagrate (with a burst of flame) in the vicinity of 150° C. Analytical values for these crystals may be as follows: $^1$H NMR (acetone-$d_6$): 10.8 (very broad); $^{13}$C NMR (acetone-$d_6$): 151.2, 152.3; IR (ATR): 3400-2900 (broad absorption), 2192 (weak, $N_3$), 2163 (medium, $N_3$), 1690, 1593 (strong), 1560, 1496, 1419, 1304 (strong), 1260 (strong), 1118, 1098, 994 cm$^{-1}$; and TLC (chloroform/methanol/acetic acid, 40/8/1, v/v/v as developer): $R_F$=0.27 (visualized with uv light).

Example 7

The Making of Azidonitraminotriazole (3-azido-N-nitro-1H-1,2,4-triazol-5-amine), mono-potassium salt (8)

In yet another exemplary embodiment of the present invention, azidonitraminotriazole (7) (approximately 0.17 g, 0.001 mole) may be stirred in about 7 ml of distilled water, while about 2 ml of potassium hydroxide solution (containing about 0.001 mole of KOH) is slowly added, dropwise. The postassium hydroxide may, for example, may be prepared by dissolving approximately 0.67 g of about 85% KOH in about 20 ml of distilled water. The reaction solution may be filtered to remove a very small amount of insoluble material, before the water is removed from the filtrate under reduced pressure. The resulting crystalline residue is washed with about 10 ml of chloroform to give 0.21 g (100%) of light orange crystals. The light orange crystals may be stirred with about 1.5 ml of methanol at about 25° C. for about 5 minutes before the crystals (approximately 0.18 g, 86%) are removed by filtration and washed with chloroform. The resulting product, cream colored crystals with an orange tint, may be stirred with methanol (about 2 ml) at about 25° C. for about one hour to give approximately 0.16 g of cream-colored crystals of the azidonitraminotriazole (3-azido-N-nitro-1H-1,2,4-triazol-5-amine), mono-potassium salt (8). When heated, the crystals may explode in the vicinity of 195° C. Analytical values for these crystals may be as follows: $^1$H NMR (DMSO-$d_6$): 12.72 (s); and $^{13}$C NMR (DMSO-$d_6$): 154.2, 157.3; IR (ATR): 3613, 3400-3000 (broad), 2146 (medium, $N_3$), 1529, 1508, 1431, 1344 (strong), 1259, 1230, 1099, 1003, 858, 740 cm$^{-1}$. A sample of the crystals, dried in a vacuum desiccator over Drierite for 18 hours, exhibited no change in the IR spectrum.

Example 8

The Making of Azidonitraminotriazole (3-azido-N-nitro-1H-1,2,4-triazol-5-amine), di-potassium salt In yet another exemplary embodiment of the present invention, azidonitraminotriazole (7) (approximately 0.085 g, 0.0005 mole) may be stirred in about 2 ml of methanol. A solution of approximately 0.08 g of about 85% potassium hydroxide in about 1 ml of methanol (containing approximately 0.0012 mole KOH) may be added to the stirred solution of azidonitraminotriazole in methanol. The resulting mixture, containing a precipitated salt, may be stirred for about an additional 15 minutes before the salt is removed by filtration and washed twice with about 0.5 ml of methanol and 4× with about 1 ml of chloroform to give approximately 0.09 g (75%) of 3-azido-N-nitro-1H-1,2,4-triazol-5-amine, di-potassium salt, as cream-colored crystals. When heated, these crystals may explode in the vicinity of 190° C. Analytical values for these crystals may be as follows: $^1$H NMR (DMSO-$d_6$/$D_2$O, 90/10): no peaks; and $^{13}$C NMR (DMSO-$d_6$/$D_2$O, 90/10): 160.1, 167.6; IR (ATR): 3661, 3400-3000 (broad), 2144 (medium, $N_3$), 1427, 1402, 1337 (medium strong), 1294 (strong), 1102, 1025, 1003, 863 cm$^{-1}$. A sample of these crystals, dried in a vacuum desiccator over Drierite for 18 hours, may exhibit a changed IR spectrum (mainly in the OH and $N_3$ region), where absorption in the OH region is essentially gone and the $N_3$ absorption is now two peaks at 2168 and 2151 cm$^{-1}$, with approximately equal intensities.

Example 9

The Method of Making Azidoaminotriazole (5-azido-2H-[1,2,4]triazol-3-ylamine), Hydrochloric Acid Salt Hydrate In yet another exemplary embodiment of the present invention, azidoaminotriazole (5-azido-2H-[1,2,4]triazol-3-ylamine) (4) (approximately 50 mg) may be stirred in about 5 ml of water, while the mixture is acidified by the slow addition of 1N HCl. All material dissolved and the water may be allowed to evaporate to yield a crystalline residue (approximately 60 mg). Analytical values for this crystalline residue may be as follows: IR (ATR): 3383, 3256, 3096, 2951, 2719, 2151 ($N_3$, medium strong), 1685 (strong), 1593, 1522, 1358, 1201, 1049, 1009, 873, 801, 757, 718 cm$^{-1}$. Single crystal X-ray diffraction analysis shows the product to be the azidoaminotriazole, hydrochloric acid salt hydrate. Analysis: Calculated for $C_2H_6ClN_7O$: C, 13.38; H, 3.37; C119.74, N, 54.60. Found: C, 13.85; H, 3.33; Cl, 19.88, N, 55.43.

Examples 10 and 11 generally relate to the method of making alkali metal salts of nitrosoguanazine.

Example 10

The Method of Making Nitrosoguanazine ($N^3$-nitroso-4H-1,2,4-triazol-3,4,5-triamine), Sodium Salt Hydrate (5a)

In yet another exemplary embodiment of the present invention, nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) (2a) (approximately 0.92 g, 3.2 mmol) may be stirred in about 15 ml of distilled water at room temperature, while slowly adding, dropwise, a solution of sodium hydroxide (approximately 0.27 g, 6.7 mmole) in about 9 ml of water. At the end of the addition, essentially all material may be dissolved. A small amount of additional dilute sodium hydroxide may slowly be added as necessary to give complete solution. The water may be evaporated from the solution to yield approximately 1.20 g of a yellow-orange solid that was stirred for a short time with about 5 ml of methanol. An insoluble yellow orange salt may then be removed by filtration for a yield of approximately 0.77 g. Methylene chloride (about 10 ml) may then be added to the filtrate to yield an additional 0.30 g of the insoluble yellow orange salt, bringing the total yield to approximately 1.07 g (91%). Analytical values for this insoluble yellow orange salt may be as follows: $^{13}C$ NMR ($D_2O$): 154.72, 154.99; and IR (ATR): 3310, 3109, 1660 (strong), 1620, 1580, 1560, 1499, 1330, 1282, 1239 (strong), 1143, 983, 944, 904, 890, 748, 720, 696 $cm^{-1}$. Differential Scanning Calorimetry (20° C./min): Endotherm: 131; Onset: 259; Peak: 265. Single crystal X-ray diffraction analysis shows the insoluble yellow orange salt to be the nitrosoguanazine ($N^3$-nitroso-4H-1,2,4-triazol-3,4,5-triamine), sodium salt hydrate (5a). Analysis: Calculated for $C_2H_6N_7NaO_2$: C, 13.12; H, 3.30; N, 53.55; Na, 12.56. Found: C, 12.92; H, 3.66; N, 51.44, Na, 12.64.

Example 11

The Method of Making Nitrosoguanazine ($N^3$-nitroso-4H-1,2,4-triazol-3,4,5-triamine), Potassium Salt (5b)

In yet another exemplary embodiment of the present invention, nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) (2a) (approximately 0.90 g, 3.15 mmole) may be stirred in about 15 ml of distilled water at room temperature, while slowly adding, dropwise, a solution of approximately 85% potassium hydroxide pellets (approximately 0.43 g, 6.42 mmole) in about 7 ml of water. At the end of the addition, essentially all material may be dissolved. A small amount of additional dilute potassium hydroxide may be slowly added as necessary to give complete solution. The water may be evaporated from the solution to give about 1.27 g of a yellow-orange solid that may be washed 4× with about 3 ml of methanol to yield approximately 1.04 g (91%) of a yellow orange salt. Analytical values for this yellow orange salt may be as follows: $^{13}C$ NMR ($D_2O$): 154.88, 155.00; and IR (ATR): 3319, 3131, 1657, 1631, 1574, 1518, 1491, 1276, 1244, 1143, 1038, 956, 889, 723, 701 $cm^{-1}$. Differential Scanning Calorimetry (20° C./min): Onset: 228; Peak: 247. Single crystal X-ray diffraction analysis shows the yellow orange salt to be the nitrosoguanazine ($N^3$-nitroso-4H-1,2,4-triazol-3,4,5-triamine), potassium salt (5b). Analysis: Calculated for $C_2H_4KN_7O$: C, 13.26; H, 2.23; K, 21.58; N, 54.11. Found: C, 13.51; H, 2.70; K, 20.99; N, 52.92.

Examples 12-14 generally relate to the method of making copper salt complexes of nitrosoguanazine ($N^3$-nitroso-4H-1,2,4-triazol-3,4,5-triamine).

Example 12

The Method of Making Nitrosoguanazine ($N^3$-nitroso-4H-1,2,4-triazol-3,4,5-triamine) Copper Salt Complex from Copper Nitrate In yet another exemplary embodiment of the present invention, nitrosoguanazine ($N^3$-nitroso-4H-1,2,4-triazol-3,4,5-triamine) potassium salt (5b) (approximately 0.08 g, 0.44 mmole) in about 1 ml of water may be stirred at room temperature, while a solution containing approximately 0.10 g (0.43 mmole) of copper (II) nitrate hemipentahydrate in about 1 ml of water is added, dropwise. A brownish black precipitate may immediately form and may eventually turn to a green precipitate as more copper nitrate solution is added. The mixture may be stirred at room temperature for about 15 minutes before being cooled to about 5° C. for about 15 minutes. The mixture may then be filtered and the product washed 3× with about 1 ml of ice water to yield approximately 0.10 g of a green solid. Analytical values for this green solid may be as follows: IR (ATR): 3312, 1661 (strong), 1623, 1544, 1503, 1390-1318 (very strong), 1166, 1138, 1080, 1070, 1046, 918, 820, 747, 726 $cm^{-1}$. Differential Scanning Calorimetry (20° C./min): Onset: 218; Peak: 231. Single crystal X-ray diffraction analysis shows the green solid to be a nitrosoguanazine ($N^3$-nitroso-4H-1,2,4-triazol-3,4,5-triamine) copper salt complex, containing three $Cu^{2+}$ ions, three nitrosoguanazine anions, two nitrate anions, one hydroxide anion and two water molecules.

Example 13

The Method of Making Nitrosoguanazine ($N^3$-nitroso-4H-1,2,4-triazol-3,4,5-triamine) Copper Salt Complex from Copper Perchlorate In yet another exemplary embodiment of the present invention, nitrosoguanazine ($N^3$-nitroso-4H-1,2,4-triazol-3,4,5-triamine) potassium salt (5b) (approximately 0.09 g, 0.49 mmole) in about 1 ml of distilled water may be stirred at room temperature, while a solution containing approximately 0.18 g (0.44 mmole) of copper (II) perchlorate hexahydrate in 1 about ml of distilled water is added, dropwise. A brownish black precipitate may immediately form and may eventually turn to a green precipitate as copper perchlorate solution is added. This mixture may be stirred at room temperature for about 15 minutes before it is cooled to about 5° C. for about 15 minutes. The precipitate may be filtered and the product may then be washed with about 1 ml of ice water to yield approximately 0.10 g of a green solid. Analytical values for this green solid may be as follows: IR (ATR): 3335, 1665 (strong), 1557, 1505, 1388, 1357, 1080 (very strong), 921, 726 $cm^{-1}$. Differential Scanning Calorimetry (20° C./min): Onset: 206; Peak: 232.

Example 14

The Method of Making Nitrosoguanazine ($N^3$-nitroso-4H-1,2,4-triazol-3,4,5-triamine) Copper Salt Complex from Copper Sulfate In yet another exemplary embodiment of the present invention, nitrosoguanazine ($N^3$-nitroso-4H-1,2,4-triazol-3,4,5-triamine) potassium salt (5b) (approximately 0.16 g, 0.88 mmole) in about 1 ml of water was stirred at room temperature, while a solution containing approximately 0.23 g (0.92 mmole) of copper (II) sulfate pentahydrate in about 1 ml of water was added, dropwise. A brownish black precipitate may immediately form and may eventually turn to a green precipitate as more copper sulfate solution is added. The mixture may be stirred at room temperature for about 15 minutes before it is cooled to about 5° C. for about 15 minutes. The mixture may then be filtered and the product may be washed 3× with about 1 ml of ice water to yield 0.21 g of a green solid. Analytical values for this green solid may be as follows: IR (ATR): 3321, 1657, 1626, 1549, 1504, 1386, 1324, 1100-1040 (very strong), 972, 920, 746, 724 cm$^{-1}$.

Examples 15-17 generally relate to the method of making 4,6-diazido-N-nitro-1,3,5-triazin-2-amine (11a) and its cesium (11b) and rubidium (11c) salts, respectively.

Example 15

A Method for Making
4,6-diazido-N-nitro-1,3,5-triazin-2-amine (11a)

In yet another exemplary embodiment of the present invention, nitric acid (100%, about 56 ml) may be placed in a 250 ml beaker and chilled in an ice bath to about 1° C. A starting material, 6-amino-2,4-diazido-[1,3,5]-triazine (10) (approximately, 4.27 g, 23.98 mmol), may be added as a solid in portions over about 15 minutes to the nitric acid, while the temperature is maintained at or below about 3° C. After the starting material is added, the resulting yellow mixture may be stirred for about 30 minutes at an ice bath temperature. The yellow mixture may then be removed from the ice bath and allowed to stand overnight at ambient temperature. The yellow mixture may be quenched by pouring it onto 520 ml of ice, giving about 400 ml of a liquid volume. A precipitate may form on stirring for about 45 minutes. The precipitate may be filtered over a medium frit and washed with ice water, giving a white material. The white material may then be dried in a drying oven at about 65° C. to yield approximately 3.26 g (14.61 mmol, 61% yield) of the desired 4,6-diazido-N-nitro-1,3,5-triazin-2-amine (11a). Analytical values for this white material may be as follows: $^1$H NMR (DMSO-d$_6$): 12.10 (bs); $^{13}$C NMR (DMSO-d$_6$): 150.39, 158.49, 163.44, 163.52, 170.41; and IR: 2183, 2153, 1623, 1553 (strong), 1393, 1333 (strong), 1279 (strong), 1192, 1159, 1073, 1016, 968, 808, 701 cm$^{-1}$. Differential Scanning Calorimetry (20° C./min): Onset: 175; Peak: 179.

Example 16

The Method of Making 4,6-diazido-N-nitro-1,3,5-triazin-2-amine, Cesium Salt (11b)

In yet another exemplary embodiment of the present invention, 4,6-diazido-N-nitro-1,3,5-triazin-2-amine (11a) (approximately 5.0 g, 22.42 mmol) may be dissolved in about 130 ml of methyl alcohol by heating slightly in a hot water bath. Cesium hydroxide (approximately 1.05 eq., 3.95 g) may be dissolved in about 10 ml of methyl alcohol and added quickly to the solution of 4,6-diazido-N-nitro-1,3,5-triazin-2-amine (11a). A white precipitate may quickly form and the mixture may be stirred for about an additional 15 minutes. The white precipitate may be filtered over #1 Whatman paper and washed twice with methyl alcohol. The resulting material may then be dried at room temperature overnight to yield approximately 4.57 g (12.87 mmol) of the 4,6-diazido-N-nitro-1,3,5-triazin-2-amine, cesium salt (11b) (approximately 60% yield), as a white crystalline solid. Analytical values for this white crystalline solid may be as follows: IR: 2191, 2134, 1573, 1499, 1399, 1372, 1346, 1259 (strong), 1231, 1195, 1170, 1013, 974, 805, 779, 721 cm$^{-1}$. Differential Scanning Calorimetry (20° C./min): Endotherm: 178: Onset: 182; Peak: 223.

Example 17

The Method of Making
4,6-diazido-N-nitro-1,3,5-triazin-2-amine, Rubidium Salt (11c)

In yet another exemplary embodiment of the present invention, 4,6-diazido-N-nitro-1,3,5-triazin-2-amine (11a) (approximately 6.0 g, 26.91 mmol) may be dissolved in about 160 ml of methyl alcohol by heating slightly in a hot water bath. Rubidium hydroxide (1.1 eq., 3.50 ml) may be dissolved in about 20 ml of methyl alcohol and added quickly to the solution of 4,6-diazido-N-nitro-1,3,5-triazin-2-amine (11a). A white precipitate may quickly form and the mixture may be stirred for about an additional 40 minutes. The white precipitate may be filtered over #1 Whatman paper and washed three times with methyl alcohol. The resulting material may then be dried at 65° C. for about 15 minutes and then at room temperature overnight to yield approximately 4.1 g (13.31 mmol) of the 4,6-diazido-N-nitro-1,3,5-triazin-2-amine, rubidium salt (11c) (approximately 50% yield), as a white crystalline solid. Analytical values for this white crystalline solid may be as follows: $^{13}$C NMR (DMSO-d$_6$): 150.46, 158.51, 163.51; and IR: 2195, 2137, 1573, 1501, 1398, 1374, 1347, 1262 (strong), 1233, 1190, 1170, 1018, 975, 804, 780, 722 cm$^{-1}$. Differential Scanning Calorimetry (20° C./min): Endotherm: 187: Onset: 190; Peak: 214.

Because many varying and different exemplary embodiments may be made with the scope of the inventive concepts taught herein, and because many modifications may be made in the exemplary embodiments detailed herein in accordance with the descriptive requirements of the law, it is to be understood that the detailed descriptions herein are to be interpreted as illustrative and not in a limiting sense.

Finally, the numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding

What is claimed is:

1. A method of making azidoaminotriazole (5-azido-2H-[1,2,4]triazol-3-ylamine) from guanazine ([1,2,4]triazole-3,4,5-triamine), comprising:
    dissolving 1 equivalent of guanazine in water to form a first solution;
    adding approximately 1 equivalent of sodium nitrite to the first solution to form a second solution;
    slowly adding approximately 2 or more equivalents of acetic acid to the second solution to form a third solution;
    allowing a reaction to occur that forms a mixture and filtering the mixture to obtain a filtrate;
    extracting the filtrate with ethyl acetate; and removing the ethyl acetate solvent to yield the azidoaminotriazole.

2. The method of claim 1, wherein the azidoaminotriazole has a melting point of about 160-165° C. and a yield of approximately 37%.

3. A method of making a dimer of nitrosoguanazine ($N^3$-[(1E)-3-(4,5-diamino-4H-1,2,4-triazol-3-yl)-1,2-dioxidotriaz-1-enyl]-4H-1,2,4-triazole-3,4,5-triamine), comprising:
dissolving 1 equivalent of guanazine ([1,2,4]triazole-3,4,5-triamine) in water to form a first solution;
adding approximately 1 equivalent of sodium nitrite to the first solution to form a second solution;
slowly adding approximately 1 equivalent of acetic acid to the second solution to form a third solution;
allowing a reaction to occur that forms a mixture and filtering the mixture to isolate a precipitate; and
washing the precipitate with cold water to yield the dimer of the nitrosoguanazine,
wherein the dimer of nitrosoguanazine has a melting point of about 143° C.

4. A compound which is a dimer of nitrosoguanazine ($N^3$-[(1E)-3-(4,5-diamino-4H-1,2,4-triazol-3-yl)-1,2-dioxidotriaz-1-enyl]-4H-1,2,4-triazole-3,4,5-triamine).

5. A method of making azidoaminotriazole (5-azido-2H-[1,2,4]triazol-3-ylamine) from nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) in water, comprising:
adding nitrosoguanazine to the water and slowly heating the mixture;
filtering the mixture to obtain a filtrate;
extracting the filtrate with ethyl acetate; and
removing the ethyl acetate to yield crystals of azidoaminotriazole.

6. The method of claim 5, wherein the crystals of azidoaminotriazole are essentially pure by $^1$HNMR analysis and have a melting point of about 175° C.

7. A method of making azidoaminotriazole (5-azido-2H-[1,2,4]triazol-3-ylamine) from nitrosoguanazine dimer ($N^3$-[(1E)-3-(4,5-diamino-4H-1,2,4-triazol-3-yl)-1,2-dioxidotniaz-1-enyl]-4H-1,2,4-triazole-3,4,5-triamine) in water, comprising:
adding nitrosoguanazine dimer to the water and slowly heating the mixture;
filtering the mixture to obtain a filtrate; and
removing volatiles from the filtrate under reduced pressure to yield crystals of azidoaminotriazole.

8. The method of claim 7, wherein the crystals of azidoaminotriazole are essentially pure by $^1$HNMR analysis and have a melting point of about 175° C.

9. A method of making azidoaminotriazole (5-azido-2H-[1,2,4]triazol-3-ylamine) from nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) in water and acetic acid, comprising:
adding 1 equivalent of nitrosoguanazine to the water to form a first mixture;
adding approximately 0.5 equivalents of acetic acid to the first mixture to form a second mixture that is slowly heated;
filtering the second mixture;
washing the filter pad with warm water; and
removing volatiles under reduced pressure from the filtrate to yield crystals of azidoaminotriazole.

10. A method of making a nitric acid salt of azidoaminotriazole (5-azido-2H-[1,2,4]triazol-3-ylamine), comprising:
adding azidoaminotriazole to water to form a mixture;
slowly adding dilute nitric acid to the mixture until all materials are dissolved; and
evaporating the water to yield crystals of the nitric acid salt of azidoaminotriazole.

11. A method of making a hydrochloric acid salt hydrate of azidoaminotriazole (5-azido-2H-[1,2,4]triazol-3-ylamine), comprising:
adding azidoaminotriazole to water to form a mixture;
slowly adding 1 N HCl to the mixture until all materials are dissolved; and
evaporating the water to yield crystals of the hydrochloric acid salt hydrate of azidoaminotriazole.

12. An energetic compound which is selected from the group consisting of 5-azido-2H-[1,2,4]triazol-3-ylamine, its nitric acid salt and a hydrochloric acid salt hydrate.

13. A method of making azidonitraminotriazole (3-azido-N-nitro-1H-1,2,4-triazol-5-amine) from azidoaminotriazole (5-azido-2H-[1,2,4]triazol-3-ylamine) nitric acid salt, comprising:
adding the azidoaminotriazole nitric acid salt to a concentrated solution of sulfuric acid to form a mixture;
adding the mixture to water and extracting the yellow aqueous solution with ethyl acetate to give extracts;
drying and removing volatiles from the extracts to obtain a yellow-orange solid; and
stirring the yellow-orange solid in chloroform to yield the azidonitraminotriazole.

14. The method of claim 13, further comprising:
stirring the azidonitraminotriazole in water to remove insoluble impurities; and removing the water to yield yellow-orange crystals of azidonitraminotriazole.

15. A method of making azidonitraminotriazole (3-azido-N-nitro-1H-1,2,4-triazol-5-amine), mono-potassiurn salt, comprising:
adding azidonitraminotriazole to water to form a mixture;
slowly adding approximately 1 equivalent of potassium hydroxide in a solution to the mixture; and
filtering the mixture and removing volatiles to obtain a crystalline residue.

16. The method of claim 15, further comprising:
washing the crystalline residue with chloroform to obtain light orange crystals; and
stirring the light orange crystals with methanol and washing the light orange crystals with chloroform to obtain cream colored crystals of azidonitraminotriazole (3-azido-N-nitro-1H-1,2,4-triazol-5-amine), mono-potassium salt.

17. A method of making azidonitraminotriazole (3-azido-N-nitro-1H-1,2,4-triazol-5-amine), di-potassium salt, comprising:
adding azidonitraminotriazole to methanol to form a mixture;
slowly adding at least approximately 2 equivalents of potassium hydroxide in a solution to the mixture; and
filtering the mixture to isolate a crystalline product.

18. An energetic compound which is selected from the group consisting of azidonitraminotriazole (3-azido-N-nitro-1H-1,2,4-triazol-5-amine), its mono-potassium salt, and di-potassium salt.

19. A method of making nitrosoguanazine ($N^3$-nitroso-4H-1,2,4-triazol-3,4,5-triamine), sodium salt hydrate, comprising:
adding 1 equivalent of nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) to water to form a mixture;

slowly adding approximately 2 equivalents of a solution of sodium hydroxide until all materials are dissolved;

evaporating the water to yield a yellow-orange solid that is mixed with methanol; and filtering the methanol mixture to yield nitrosoguanazine, sodium salt hydrate.

20. The method of claim 19, further comprising:

adding methylene chloride to a filtrate of the methanol mixture; and removing solvents to yield an additional amount of the sodium salt hydrate of nitrosoguanazine.

21. A method of making nitrosoguanazine ($N^3$-nitroso-4H-1,2,4-triazol-3,4,5-triamine), potassium salt, comprising:

adding 1 equivalent of nitrosoguanazine dimer ($N^3$-[(1E)-3-(4,5-diamino-4H-1,2,4-triazol-3-yl)-1,2-dioxidotriaz-1-enyl]-4H-1,2,4-triazole-3,4,5-triamine) to water to form a mixture;

slowly adding approximately 2 equivalents of a solution of potassium hydroxide until all materials are dissolved;

evaporating the water to yield a yellow-orange solid that is washed with methanol; and filtering the methanol mixture to yield nitrosoguanazine, potassium salt.

22. A compound which is selected from the group consisting of a nitrosoguanazine ($N^3$-nitroso-4H-1,2,4-triazol-3,4,5-triamine) alkali metal salt and its salt hydrate.

23. A method of making a nitrosoguanazine ($N^3$-nitroso-4H-1,2,4-triazol-3,4,5-triamine), metal salt complex, comprising:

adding 1 equivalent of nitrosoguanazine potassium salt to water to form a mixture;

slowly adding approximately 1 equivalent of a metal salt to the mixture;

filtering the mixture to isolate a precipitate; and washing the precipitate with ice water to yield the metal salt complex of nitrosoguanazine, wherein the metal salt is selected from the group consisting of copper salt, iron salt, cobalt salt, nickel salt, and zinc salt.

24. The method of claim 23, wherein the copper salt is selected from the group consisting of copper nitrate, copper perchlorate, and copper sulfate.

25. A laser-sensitive initiating compound which is a metal salt complex of nitrosoguanazine ($N^3$-nitroso-4H-1,2,4-triazol-3,4,5-triamine).

26. A method of making 4,6-diazido-N-nitro-1,3,5-triazin-2-amine, comprising:

slowly adding 6-amino-2,4-diazido-[1,3,5]-triazine as a solid to chilled nitric acid to form a mixture; and filtering the mixture to obtain the 4,6-diazido-N-nitro-1,3,5-triazin-2-amine as a precipitate.

27. The method of making an alkali metal salt of 4,6-diazido-N-nitro-1,3,5-triazin-2-amine, comprising:

adding 1 equivalent of 4,6-diazido-N-nitro-1,3,5-triazin-2-amine to methyl alcohol to obtain a solution;

adding approximately 1.05-1.10 equivalents of an alkali metal hydroxide, dissolved in methyl alcohol, to the solution; and obtaining a precipitate from the solution that is washed with methyl alcohol and dried to yield the alkali metal salt of 4,6-diazido-N-nitro-1,3,5-triazin-2-amine.

28. The method of claim 27, wherein the alkali metal hydroxide is selected from the group consisting of cesium hydroxide and rubidium hydroxide.

29. An energetic compound which is selected from the group consisting of 4,6-diazido-N-nitro-1,3,5-triazin-2-amine and its alkali metal salt.

* * * * *